United States Patent [19]
Brown

[11] Patent Number: 6,080,757
[45] Date of Patent: *Jun. 27, 2000

[54] ANTIBIOTIC QUINOLONES AND DERIVATIVES

[75] Inventor: Matthew F. Brown, Pawcatuck, Conn.

[73] Assignee: Pfizer Inc, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/864,573

[22] Filed: May 28, 1997

Related U.S. Application Data

[60] Provisional application No. 60/019,227, Jun. 6, 1996.

[51] Int. Cl.$^7$ .......................... A61K 31/47; A01N 43/42; C07D 215/36; C07D 215/16
[52] U.S. Cl. .......................... 514/312; 546/153; 546/154
[58] Field of Search ................... 546/153, 154, 546/312

[56] References Cited

U.S. PATENT DOCUMENTS

| | | | |
|---|---|---|---|
| 5,112,852 | 5/1992 | Crossley et al. | 514/299 |
| 5,194,617 | 3/1993 | Minowa et al. | 546/153 |

FOREIGN PATENT DOCUMENTS

| | | | |
|---|---|---|---|
| 374765 | 6/1990 | European Pat. Off. | C07D 215/233 |
| 407192 | 1/1991 | European Pat. Off. | C07D 215/233 |
| 412848 | 2/1991 | European Pat. Off. | C07D 215/233 |
| 3520229 | 12/1986 | Germany | C07D 491/044 |
| 7189 | 1/1995 | Japan . | |
| 9207468 | 5/1992 | WIPO | A01N 43/90 |
| 9528929 | 11/1995 | WIPO . | |

OTHER PUBLICATIONS

Horiuchi et al., "Reaction of 1,2,34,-Tetrahydroquinazolin-4-ones with Acid Anhydride," Chem. Pharm. Bull. vol. 29, No. 11, pp. 3130-3133, 1981.

Coppola, "The Chemistry of 2H-3,1-Benzoxazine-2, 4(1H)-dione," Synthesis, vol. 1, pp. 81-84, 1988.

Potts et al., "Mesoionic Compounds. XXXIII. Thermal Rearrangement of 4H-1,3-Thiazinium Betaines to 4-Quinolones," J. Org. Chem., vol. 40, No. 18, pp. 2596-2600, 1975.

Evans, et al., J. of Antibiotics, vol. XXI, 952 (1978).
Hashimoto, et al., Chem. Pharm Bull., 15, 718 (1967).
Fuson, et al., J. Am. Chem. Soc., 68, 1270 (1946).
Chong, et al., Tetrahedron Letters, 27, 5323 (1986).
Raban, et al., J. Org. Chem., 55, 4311 (1990).
Roitman, et al., J. Agric. Food Chem., 38, 538 (1990).
Kappe, et al., J. Chem. Soc., Chem. Commun., 485 (1992).
Parsonnet et al., "Helicobacter Pylori Infection and the Risk of Gastric Carcinoma," The New England Journal of Medicine vol. 325, No. 16, pp. 1127-1131, Oct. 1991.
Kato et al., "Photochemical and Thermal Reactions of Heterocycles," J. Chem. Soc. Perkin Trans. I, 1988, pp. 189-192.
Ahsan et al., "Quinolone and Acridone Alkaloids from Boronia Lanceolata," Phytochemistry, 1993, vol. 33, No. 6, pp. 1507-1510.
C.A., 109:190215 (1968).
C.A., 106:102201 (1987).
C.A., 98:107134 (1983).

*Primary Examiner*—Mukund J. Shah
*Assistant Examiner*—Tamthom N. Truong
*Attorney, Agent, or Firm*—Peter C. Richardson; Paul H. Ginsburg; Roy F. Waldron

[57] ABSTRACT

A compound of the formula I

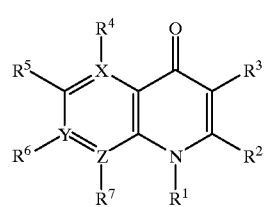

or a pharmaceutically acceptable salt or hydrate thereof, wherein X, Y, Z and $R^1$ to $R^7$ are as defined herein, are inhibitors of *H. pylori* and therefore of use in the treatment and prevention of peptic ulcers, gastritis, dyspepsia, and gastric cancer.

2 Claims, No Drawings

ANTIBIOTIC QUINOLONES AND DERIVATIVES

This application claims the benefit of provisional application No. 60/019,227 filed Jun. 6, 1996.

BACKGROUND OF THE INVENTION

This invention relates to novel quinolones and naphthyridones, pharmaceutical compositions containing them, and methods of using them in the treatment of *H. pylori*.

*Helicobacter pylori* is a Gram-negative spiral bacterium discovered in 1982 which has been found to play a role in peptic ulcer disease and chronic type-B gastritis. The bacterium has also been linked to non-ulcer dyspepsia and gastric cancer. The eradication of the bacterium by antibiotic therapy has ben shown to cure peptic ulcers allowing sufferers thereof to discontinue chronic acid-lowering therapies. Effective eradication of *H. pylori* has to date involved the use of one or more broad spectrum antibiotics often combined with an acid lowering agent.

SUMMARY OF THE INVENTION

The present invention relates to a compound of the formula

I or a pharmaceutically acceptable salt or hydrate thereof, wherein
- $R^1$ is hydrogen, $C_1$–$C_3$ alkyl, or phenyl which may be substituted by one to three of halo, $C_1$–$C_6$ alkyl, $C_1$–$C_6$ alkoxy, nitro, amino, $C_1$–$C_6$ alkylamino, or di($C_6$–$C_6$-alkyl)amino;
- $R^2$ is $C_1$–$C_{10}$ alkyl, ($C_1$–$C_{10}$ alkyl)phenyl, $C_2$–$C_{10}$ alkenyl, ($C_2$–$C_{10}$ alkenyl)phenyl, $C_2$–$C_{10}$ alkynyl, ($C_2$–$C_{10}$ alkynyl)phenyl, phenyl, naphthyl, furyl, thiophenyl or pyridyl, wherein each of the cyclic groups may be substituted by halogen, $C_1$–$C_6$ alkyl, $C_1$–$C_6$ alkoxy, carboxy, phenyl, amino, $C_1$–$C_6$ alkylamino or di($C_1$–$C_6$ aklyl)amino;
- $R^3$ is $C_1$–$C_4$ alkyl, phenyl or benzyl, said phenyl or the phenyl in said benzyl optionally substituted by one to three of halogen, $C_1$–$C_6$ alkyl, $C_1$–$C_6$ alkoxy, nitro, amino, $C_1$–$C_6$ alkylamino or di($C_1$–$C_6$ alkyl)amino;
- $R^4$, $R^5$, $R^6$ and $R^7$ are each independently hydrogen, $C_1$–$C_3$ alkyl, $C_1$–$C_3$ alkoxy, halogen, nitro, amino, $C_1$–$C_6$ alkylamino, or di($C_1$–$C_6$ alkyl) amino, except that $R^4$, $R^6$ and $R^7$ are not present when X, Y and Z, respectively, are nitrogen; and
- X, Y and Z are independently carbon or nitrogen;
- with the proviso that when X, Y and Z are each carbon and $R^4$, $R^5$, $R^6$ and $R^7$ are each hydrogen, then
  (1) if $R^3$ is methyl, $R^2$ is not $C_6$–$C_{10}$ alkenyl, propyl or phenyl, and
  (2) if $R^3$ is ethyl, $R^2$ is not phenyl or $C_6$–$C_{10}$ alkenyl.

The compounds of the invention may exist in several polymorphic forms. The invention includes all polymorphs of the compounds of the invention, as defined below.

In preferred embodiments, $R^1$ is hydrogen or methyl, $R^2$ is $C_2$–$C_6$ alkenyl, ($C_1$–$C_{10}$ alkyl)phenyl, $C_3$–$C_6$ cycloalkyl, ($C_3$–$C_6$ cycloalkyl)$C_1$–$C_2$ alkynyl, or phenyl, each of which may be substituted by halogen, $C_1$–$C_4$ alkyl or carboxy, $R^4$, $R^5$, $R^6$ and $R^7$ are each hydrogen or halogen, and X, Y and Z are each carbon.

In a specific embodiment, X, Y and Z are each carbon, $R^4$, $R^5$, $R^6$ and $R^7$ are each hydrogen, and $R^3$ is phenyl or benzyl each optionally substituted by one to three of halogen, $C_1$–$C_6$ alkyl, $C_1$–$C_6$ alkoxy, nitro, amino, $C_1$–$C_6$ alkylamino or di($C_1$–$C_6$ alkyl)amino.

The present invention also relates to a pharmacutical composition for the treatment or prevention of an *H. pylori* infection which comprises a compound of the formula I or a pharmaceutically acceptable salt or hydrate thereof, wherein
- $R^1$ is hydrogen, $C_1$–$C_3$ alkyl, or phenyl which may be substituted by one to three of halo, $C_1$–$C_6$ alkyl, $C_1$–$C_6$ alkoxy, nitro, amino, $C_1$–$C_6$ alkylamino, or di($C_1$–$C_6$ alkyl)amino;
- $R^2$ is $C_1$–$C_{10}$ alkyl, $C_2$–$C_{10}$ alkenyl, $C_2$–$C_{10}$ alkynyl, phenyl, naphthyl, furyl, thiophenyl or pyridyl, each of which cyclic compounds may be substituted by halogen, $C_1$–$C_6$ alkyl, $C_1$–$C_6$ alkoxy, carboxy, phenyl, amino, $C_1$–$C_6$ alkylamino or di($C_1$–$C_6$ aklyl)amino;
- $R^3$ is $C_1$–$C_4$ alkyl, phenyl or benzyl, said phenyl or the phenyl in said benzyl optionally substituted by one to three of halogen, $C_1$–$C_6$ alkyl, $C_1$–$C_6$ alkoxy, nitro, amino, $C_1$–$C_6$ alkylamino or di($C_1$–$C_6$ alkyl)amino;
- $R^4$, $R^5$, $R^6$ and $R^7$ are each independently hydrogen, $C_1$–$C_3$ alkyl, $C_1$–$C_3$ alkoxy, halogen, nitro, amino, $C_1$–$C_6$ alkylamino, or di($C_1$–$C_6$ alkyl) amino; with the proviso that when X, Y and Z are each carbon, $R^4$, $R^5$, $R^6$ and $R^7$ are each hydrogen and $R^2$ is methyl or ethyl, then $R^3$ is not $C_6$–$C_{10}$ alkenyl; in an amount effective in the treatment or prevention of said infection, and a pharmaceutically acceptable carrier.

In addition, the invention relates to a pharmaceutical composition for the treatment or prevention of an *H. pylori* infection comprising a compound of the formula I or a pharmaceutically acceptable salt or hydrate thereof, wherein
- $R^1$ is hydrogen, $C_1$–$C_3$ alkyl, or phenyl which may be substituted by one to three of halo, $C_1$–$C_6$ alkyl, $C_1$–$C_6$ alkoxy, nitro, amino, $C_1$–$C_6$ alkylamino, or di($C_1$–$C_6$ alkyl)amino;
- $R^2$ is $C_1$–$C_{10}$ alkyl, $C_2$–$C_{10}$ alkenyl, $C_2$–$C_{10}$ alkynyl, phenyl, naphthyl, furyl, thiophenyl or pyridyl, each of which cyclic compounds may be substituted by halogen, $C_1$–$C_6$ alkyl, $C_1$–$C_6$ alkoxy, carboxy, phenyl, amino, $C_1$–$C_6$ alkylamino or di($C_1$–$C_6$ aklyl)amino;
- $R^3$ is $C_1$–$C_4$ alkyl, phenyl or benzyl, said phenyl or the phenyl in said benzyl optionally substituted by one to three of halogen, $C_1$–$C_6$ alkyl, $C_1$–$C_6$ alkoxy, nitro, amino, $C_1$–$C_6$ alkylamino or di($C_1$–$C_6$ alkyl)amino;
- $R^4$, $R^5$, $R^6$ and $R^7$ are each independently hydrogen, $C_1$–$C_3$ alkyl $C_1$–$C_3$ alkoxy, halogen, nitro, amino, $C_1$–$C_6$ alkylamino, or di($C_1$–$C_6$ alkyl) amino; a pharmaceutically acceptable carrier, and another pharmaceutically acceptable antimicrobial agent or a pharmaceutically acceptable acid lowering agent.

The present invention further relates to a method for the prevention or treatment of an *H. pylori* infection in a host by administering to said host a compound of the formula I, wherein X, Y, Z, $R^1$, $R^2$, $R^3$, $R^4$, $R^5$, $R^6$, and $R^7$ are as defined immediately above, in an amount which is effective in said prevention or treatment; and to a method for the prevention or treatment of peptic ulcers, gastritis, dyspepsia, or gastric cancer in a host by administering to said host a compound of formula I, as defined immediately above, in an amount which is effective in said prevention or treatment. The treatments may include administration of another pharmaceutically acceptable antimicrobial agent or a pharmaceutically acceptable acid-lowering agent.

DETAILED DESCRIPTION OF THE INVENTION

As used herein, "halogen" includes fluoro, chloro, bromo or iodo.

As used herein, "alkyl" includes straight or branched hydrocarbon radicals, and combinations thereof, e.g. methyl, ethyl, propyl, i-propyl, i-butyl, t-butyl, etc.

As used herein, "alkyloxy" includes O-alkyl groups wherein "alkyl" is as defined above, e.g. methoxy, cyclopentyloxy, etc.

As used herein, "alkenyl" and "alkynyl" include straight or branched groups having one double bond or one or two triple bonds, respectively, or combinations thereof, e.g. butenyl, pentenyl, pentynyl, etc.

As used herein, "a pharmaceutically acceptable salt or hydrate" includes pharmaceutically acceptable salts, hydrates, pharmaceutically acceptable salts of hydrates, and hydrates of such salts.

The compounds of formula I may be prepared as set out in the following Scheme.

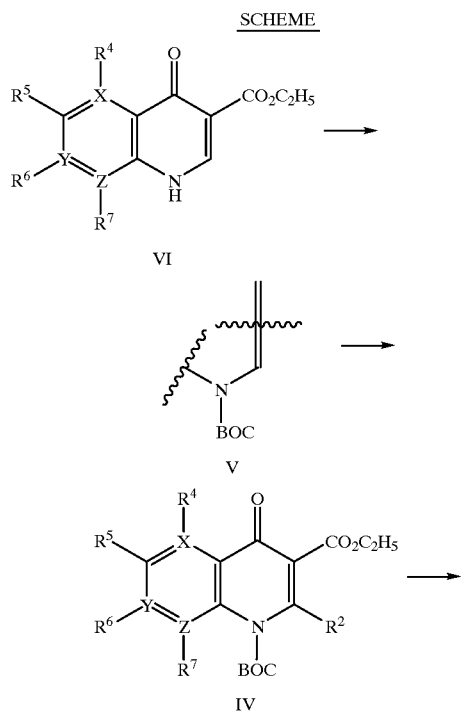

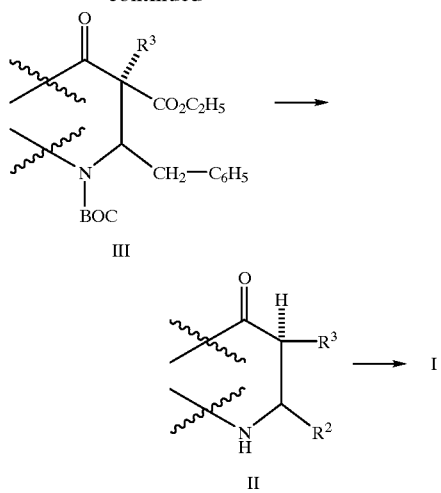

The compounds of formula VI may be prepared by methods known to the person skilled in the art.

The compound of formula V is formed on reaction of compound VI with di-t-butyl dicarbonate in the presence of a base such as triethyl amine to protect the nitrogen atom.

The group $R^2$ is introduced into compound V with a Grignard reagent containing group $R^2$, e.g. $R^2$ magnesium bromide, or $R^2Cu(CN)ZnBr$, under Grignard reaction conditions to form a compound of formula IV.

Introduction of group $R^3$ into compound IV is accomplished by reaction of compound IV in the presence of a base such as potassium carbonate, with a compound of the formula $R^3$ L wherein L is a leaving group such as halide, e.g. iodide, to form a compound of the formula III.

Removal of the two carboxylic ester groups by known methods results in a compound of the formula II. The compound of formula I is then obtained from compound II by dehydrogenation with 2,3-dichloro-5,6-dicyano-1,4-benzoquinone (DDQ).

When $R^1$ is methyl, $R^1$ may be introduced by reaction of compound I wherein $R^1$ is hydrogen with a compound of the formula $CH_3L$ wherein L is as defined above.

According to the invention, the active compound may be used in combination with a second pharmaceutically acceptable antimicrobial agent, such as nitroimidazole antibiotics, e.g. tinidazole and metronidazole; tetracyclines, e.g. tetracycline, doxycycline and minocycline; penicillins, e.g. amoxicillin, ampicillin and meziocillin; cephalosporins, e.g. cefaclor, cefadroxil, cephadrine, cefuroxime, cefuroxime axetil, cephalexin, cefpodoxime proxetil, ceftazidime and cefatriaxone; carbapenems, e.g. imipenem and meropenem; aminoglycosides, e.g. paromomycin; macrolide antibiotics, e.g. erythromycin, clarithromycin and azithromycin; lincosamide antibiotics, e.g. clindamycin; rifamycins, e.g. rifampicin; and nitrofurantoin.

Also included within the invention are combinations of the compounds of the invention as defined below with a pharmaceutical acid-lowering agent used in the treatment of acid-related disorders, such as acid pump inhibitors, e.g., omeprazole and lansoprazole, or $H_2$ antagonists, e.g., ranitidine, cimetidine, and famotidine.

The pharmaceutically acceptable acid addition salts of compounds of the formula I containing a basic nitrogen, e.g. when $R^4$ is amino, may be prepared in a conventional manner by treating a solution or suspension of the free base of the formula I with about one chemical equivalent of a pharmaceutically acceptable acid. Conventional concentration and recrystallization techniques are employed in isolating the salt.

The pharmaceutically acceptable base addition salts of compounds of formula I containing an acid group may be prepared in a conventional manner from the acid, e.g. by reaction with about one chemical equivalent of a base.

The novel compounds of the formula I or a pharmaceutically acceptable salt or hydrate thereof (the compounds of the invention) are useful in the treatment of *H. pylori* infections.

The compounds of the invention may be administered alone, but will generally be administered in admixture with a pharmaceutical carrier selected with regard to the intended route of administration and standard pharmaceutical practice. For example, they can be administered orally or in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water in a concentration of about 5 to about 5000 ppm, preferably about 25 to about 500 ppm. They can be injected parenterally, for example, intramuscularly, intravenously or subcutaneously. For parenteral administration, they are best used in the form of a sterile aqueous solution which can contain other solutes, for example, enough salt or glucose to make the solution isotonic. In the case of animals, compounds can be administered intramuscularly or subcutaneously at dosage levels of about 0.1 to about 50 mg/kg/day, preferably about 0.2 to about 10 mg/kg/day given in a single daily dose or up to 4 divided doses.

The compounds of the invention can be administered to humans for the treatment of *H. pylori* infections by either the oral or parenteral routes and may be administered orally at dosage levels of about 0.1 to about 500 mg/kg, advantageously about 0.5 to about 50 mg/kg/day given in a single dose or up to 4 divided doses. For intramuscular or intravenous administration, dose levels are about 0.1 to about 200 mg/kg/day, preferably about 0.5 to about 50 mg/kg/day. While intramuscularly administration may be a single dose or up to 4 divided doses, intravenous administration can include a continuous drip. Variations will necessarily occur depending on the weight and condition of the subject being treated and the particular route of administration chosen as will be known to those skilled in the art.

The second antimicrobial agent and the acid-lowering agent may be administered with the compounds of the invention in the same manner as discussed above for the compounds of the invention. Thus, depending on the particular agent, administration may be orally at about 0.1 to about 500 mg/kg, for instance at about 1 to 3 grams per day of second antimicrobial agent, and about 40 to 80 mg per day of the acid-lowering agent, or by injection at about 0.1 to about 200 mk/kg/day.

The activity of the compounds of the invention may be determined by the following test.

Agar Dilution of Antimicrobial 6 mg. of the compound to be evaluated is solubilized in 0.6 ml 100% dimethylsulfoxide (DMSO) and then brought up to 6 ml with sterile brucella broth and the solubility is noted. The final concentration of DMSO is 10% of the total volume. Serial 2-fold dilutions (3 ml compound+3 ml brucella broth) are then made in sterile brucella broth. A 2 ml aliquot of each broth dilution within the series is placed in separate sterile petri dishes, to which 18 ml of melted and cooled (approx. 50° C.) brucella agar supplemented with 7% horse blood is added. This yields a final 1:10 dilution of compound in agar, and a final concentration of DMSO of 1%. For example, if the highest concentration (1 st broth dilution) contains 1000 ug/ml, and is diluted 1:10 in agar, the final concentration of drug in agar is 100 ug/ml. Agar plates can be prepared one day prior to inoculating, and refrigerated overnight.

Inocula Preparation

*Helicobacter pylori* cultures are maintained on trypticase soy-5% sheep blood agar plates, and are transferred every 48 hours. *Helicobacter mustelae* cultures are maintained on the same agar, and are transferred every 48–60 hours, depending upon the extent of the growth of the previous transfer. Plates are incubated at 37° C. in GasPak jars with water-activated (10 ml) CampyPak Plus (BBL Microbio. Systems) envelopes with palladium catalyst.

Helicobacter cultures can be grown in brucella broth supplemented with 10% fetal calf serum in 10 ml volumes in deep petri dishes. The plates are incubated for 18–20 hours at 37° C. in GasPak jars with water-activated (10 ml) CampyPak Plus envelopes with palladium catalyst on a shaker at 50 rpm.

Overnight cultures (approx. $10^8$ CFU/ml) are diluted 10-fold in brucella broth (no FCS) in screwcapped tubes for use as the standard inoculum. The wells of a Steer replicator are filled with 0.8 ml of the diluted organism, and approximately $2 \times 10^4$ cells in 0.002 ml are placed on the agar surface. Inoculatd plates are placed in a GasPak jar to which water-activated (10 ml) Campy Pak Plus envelopes with palladium catalyst have been added, and incubated at 37° C. for 48 hours.

Interpretation of Results

Following incubation, all test plates are compared to a compound-free growth control plate. The MIC is the concentration which inhibits growth compared to the control plate. A thin film of growth might be visible at higher concentrations but this is discounted, and not considered the true MIC. Control organisms are also inoculated on each plate, and these are diluted 1000-fold for use as inocula. The control organisms include *Campylobacter jejuni* (#6686), and the screening cultures of *E. coli* (#51A266 and #51A470), *Enterobacter aerogenes* (#67A040), *E. cloacae* (#678009), *Providencia stuartii* (#77A013) and *P. rettgeri* (#77C025). Plates and/or inocula transfers should not be out of the microaerophilic environment longer than 2 hours. It is also recommended that all manipulations involving Helicobacter cultures be performed in a laminar flow hood to decrease the chance of contaminating the cultures with mold.

The mouse model of Lee et al., Gastroenterology, 99, 1315–23(1990) is used to predict the in vivo activity of a compound against *H. pylori* in humans.

*Helicobacter felis* is grown in brucella broth with 10% fetal bovine serum. A frozen culture is quickly thawed; the culture is checked for motility and 0.5 cc. of the thawed frozen culture is inoculated into a deep tissue culture dish containing 9.5 cc. of the brucella/serum mix. The dishes are put into a Campy Pak jar [BBL] to insure a microaerophilic atmosphere. The jar is put on a rotary shaker at 60 RPM in a 37° C. incubator. After 18 hours there should be visible turbidity. The culture is checked for purity and motility under a (phase) microscope and then pooled into a flask. Swiss-Webster female mice (18–20 g) are fasted for 18 hours before infection. The mice are infected three times on alternate days during a single week. Dosing begins two weeks after the last dose of organism. Treatments are given once per day for fourteen consecutive days. Sacrifice is about three weeks after completion of therapy. For each mouse, the stomach is excised and opened along the greater curvature. A plug (a 3 mm. tissue section) is taken from the antrum region of the stomach. The plug surface is washed, minced, and dropped into a tube with 100 microliters of urease reagent. The urease reagent is the reagent of Hazell et. al., Am. J. Gastroenterology, 82, 292–296 (1982). The urease reagent (pH 6.3–6.5) contains urea and phenol red. If Helicobacter is present, urease will break down urea producing a change of pH. Purple (alkaline) is positive for Helicobacter; red/yellow (no change) is negative. Any color change is recorded after 18 hours. There are usually twenty mice per treatment group; the percent positive for each group is recorded.

There are several methods used clinically to determine whether *Helicobacter pylori* is present in a human subject. These are employed for initial diagnosis of infection prior to treatment, as well as for determining the success of treatment in eradicating the organism from the patient.

The urea breath test involves ingestion of radiolabelled urea. *H. pylori* produces a urease enzyme which degrades urea; mammalian gastric cells do not contain this enzyme. Exhalation of labeled carbon dioxide (analyzed by mass spectrometry or radioactivity, depending on the isotope employed) therefore indicates that *H. pylori* is present.

Serology can also be used to assess infection with *H. pylori*. Detection of serum antibodies to *H. pylori*, such as IgG and IgA, is carried out using enzyme-linked immunosorbent assay (ELISA). Numerous different *H. pylori* proteins can be employed as antigens.

Endoscopy of the patient provides samples of tissue which can be cultured in a microaerophilic environment to diagnose *H. pylori* infection. Alternatively, the sample can be examined histologically by employing one of a number of stains such as Giemsa or hematoxylin-eosin. A urea test, which again takes advantage of the production of urease by *H. pylori*, can also be applied. This test relies on the formation of ammonia from the urea hydrolysis, which results in an observable change in pH.

The following Examples serve to illustrate the invention. The melting points are in ° C.

Example 1

A. 4-Oxo-4H-quinoline-1,3-dicarboxylic acid 1-t-butyl ester 3-ethyl ester

To a solution of 1H-quinolin-4-one-3-carboxylic acid ethyl ester (28 g, 129 mmol) and triethylamine (21.6 mL, 155 mmol) in dimethylformamide (DMF) (250 mL) was added di-t-butyidicarbonate [(BOC)$_2$O] (34 g, 155 mmol). The resulting solution was stirred at ambient temperature for 3 hours, then quenched with 1M aqueous hydrogen chloride and extracted with ethyl acetate (EtOAc). The combined organics were dried over magnesium sulfate and concentrated in vacuo. The crude product was purified by trituration in diethyl ether/hexanes (1:1) to give the title compound (39.5 g, 96%).

B. 2-Benzyl-4-oxo-3,4-dihydro-2H-quinoline-1,3-dicarboxylic acid-1-t-butyl ester 3-ethyl ester To a suspension of the title compound of IA. (12.3 g, 38.8 mmol) in tetrahydrofuran (175 mL) at −78° C. was added a solution of benzylmagnesium bromide in tetrahydrofuran (23.2 mL, 46.6 mmol). The solution was stirred at −78° C. for 1 hour, then warmed to ambient temperature. The reaction was quenched by addition of saturated aqueous sodium bicarbonate, then extracted with ethyl acetate, and the combined organics dried over magnesium sulfate. Concentration in vacuo, followed by chromatography (1:3 ethyl acetate:hexanes) gave the title compound (12.87 g, 81%).

C. 2-Benzyl-3-methyl-4-oxo-3,4-dihydro-2H-quinoline-1,3-dicarboxylic acid-1-t-butyl ester 3-ethyl ester To a solution of the compound of IB (1.0 g, 2.44 mmol) in DMF (5 mL) was added potassium carbonate (1.01 g, 7.33 mmol) and methyl iodide (0.46 mL, 7.33 mmol). The resulting mixture was stirred at ambient temperature for 1.5 hours, then quenched with 1M aqueous hydrogen chloride (HCl). The mixture was extracted with EtOAc, and the combined organics were dried over magnesium sulfate (MgSO$_4$). Concentration followed by chromatography on silica gal (1:5 EtOAc:Hexanes) gave the title compound (1.03 g, 100%).

D. 2-Benzyl-3-methyl-2,3dihydro-1H-quinolin-4-one

To a solution of the compound of IC, (0.98 g, 2.30 mmol) in methanol (40 mL) was added 40% aqueous potassium hydroxide (10 mL). The resulting solution was stirred at reflux for 2 hours, then cooled. The solution was neutralized with 1 M HCl, then extracted with dichloromethane (CH$_2$Cl$_2$). The combined organics were dried over MgSO$_4$ and concentrated in vacuo to give the decarboxylated intermediate as a clear oil (0.753 g) which was taken on directly to the next step. This intermediate was dissolved in CH$_2$Cl$_2$ (30 mL) to which was added trifluoroacetic acid (15 mL). The resulting solution was stirred at ambient temperature for 1 hour. The solution was treated with 2M aqueous sodium hydroxide, and extracted with CH$_2$Cl$_2$. The combined organics were dried over MgSO$_4$, and concentrated in vacuo. Chromatography on silica gel (1:4 EtOAc:Hexanes) gave the title compound (0.50 g, 93%).

E. 2-Benzyl-3-methyl-1H-quinolin-4-one

To a solution of the compound of ID (13 g, 51.8 mmol) in 10:1 dioxane:water (110 mL) was added DDQ (14.1 g, 62.1 mmol). The solution was stirred for 18 hours at ambient temperature, then diluted with saturated aqueous NaHCO$_3$. The solution was extracted with CH$_2$Cl$_2$, dried over MgSO$_4$ and concentrated in vacuo to give an orange solid. Trituration in CH$_2$Cl$_2$ followed by filtration gave the title compound (9.47 g, 73%). m.p. 285–287° C. HRMS (M+H) calcd. for C$_{17}$H$_{16}$NO: 249.1150. Found: 249.1141.

Example 2

Using the method of Example 1, the compounds shown in Table I were prepared. In some cases, the compounds were recrystallized from dimethylformamide or dimethylsulfoxide. Me stands for methyl, Bu is butyl, Et is ethyl, Pr is propyl and Bn is benzyl.

TABLE I

VIII

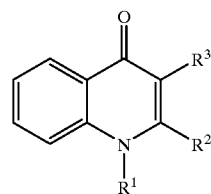

| R$^1$ | R$^2$ | R$^3$ | m.p. |
|---|---|---|---|
| H | allyl | Me | 249–254 |
| H | Bn | Me | 285–287 |
| Me | Bn | Me | 147–149 |
| H | Bn | Bu | 213–214 |

TABLE I-continued

VIII

[Structure: quinolin-4-one with R³ at position 3, R² at position 2, R¹ on N]

| R¹ | R² | R³ | m.p. |
|---|---|---|---|
| H | Bn | Et | 147–149 |
| H | Bn | Bn | 259–261 |
| Me | Bn | Et | 118–120 |
| H | Bn | n-Pr | 270–272 |
| Me | Bn | Bn | 183–185 |
| Me | Bn | n-Pr | HRMS (M + H): 292.1701 (calcd.) 292.1727 (found) |
| H | 3,7-dimethyl-n-octyl | Me | 187–188 |
| Me | 3,7-dimethyl-n-octyl | Me | oil HRMS (M + H): 314.2484 (calcd.) 314–2457 (found) |
| H | n-octyl | Me | 228–230 |
| Me | n-octyl | Me | 78–79 |
| H | o-tolyl | Me | 320–322 |
| Me | o-tolyl | Me | 175–176 |
| H | 2-phenethyl | Me | 287–288 |
| H | 2-methylbenzyl | Me | 265–268 |
| H | n-butyl | Me | HRMS (M + H): 216.1388 (calcd.) 216.1376 (found) |
| H | n-hexyl | Me | 239–240 |
| H | cyclohexyl | Me | 286–288 |
| H | cyclopentyl | Me | 292–299 |
| H | Me | Bn | 292–293 |
| Me | Me | Bn | 212–213 |
| H | m-tolyl | Me | 280–282 |
| H | p-tolyl | Me | 261–262 |
| H | Et | Me | 280–283 |
| H | 1-naphthyl | Me | 315–316 |
| H | 2-naphthyl | Me | 337–339 |
| H | 3-biphenyl | Me | 348–350 |
| H | 2-thienyl | Me | 240–242 |
| H | 4-biphenyl | Me | 305–310 |
| H | p-chlorophenyl | Me | 275–280 |
| H | mesityl | Me | 360–362 |
| H | 2-furyl | Me | 255–260 |
| H | n-pentyl | Me | 243–244 |
| H | 4-phenylbutyl | Me | 256–257 |
| H | 3-phenylpropyl | Me | 255–256 |
| H | 5-phenylpentyl | Me | 255–256 |
| H | 4-pentenyl | Me | 235–237 |
| H | 5-hexenyl | Me | 230–232 |
| H | 4-fluoro-3-methylphenyl | Me | 305–306 |
| H | cycloheptyl | Me | 293–294 |
| H | cyclooctyl | Me | 276–278 |
| H | 4-fluorobenzyl | Me | 290–293 |
| H | prenyl (3-methyl-butenyl) | Me | 232–233 |
| H | cyclohexylmethyl | Me | 350–351 |
| H | naphthylen-2-ylmethyl | Me | 340–342 |
| H | 4-t-butylphenyl | Me | 334–336 |
| H | 2-fluorobenzyl | Me | 270–272 |
| H | 3-fluorobenzyl | Me | 305–307 |
| H | 3-pentynyl | Me | 327–328 |
| H | indan-2-yl | Me | 327–328 |
| H | 3-carboxybenzyl | Me | 354–356 |
| H | 4-carboxybenzyl | Me | 399–400 |

Example 3

A. (1,1-diethoxy-propyl)-benzene

To a solution of propiophenone (20 mL, 0.15 mol) in ethanol (EtOH) (20 mL) was added triethylorthoformate (32.4 mL, 0.20 mol). A stream of HCl gas was bubbled through this solution for approximately 15 seconds, then the golden solution was stirred for 20 hours at ambient temperature. The solution was then treated with NaOMe/EtOH until basic, followed by filtration. The filtrate was concentrated by removal of the EtOH in vacuo. The product was isolated via vacuum distillation to give the title compound (22.2 g, 71%). $^1$H NMR (300 MHz, CDCl$_3$)δ7.51–7.47 (m, 2H), δ7.36–7.23 (m, 3H), δ3.47–3.17 (m, 4H), δ1.92 (quartet, J=7.5 Hz, 2H), δ1.20 (t, J=7.1 Hz, 6H), δ0.57 J=7.5 Hz, 3H).

B. 6-chloro-3-methyl-2-phenyl-1H-quinolin-4-one

To a mixture of 2-amino-5-chloro-benzoic acid (0.82 g, 4.80 mmol) in Dowtherm A (20 mL), was added the compound of Step A (1.0 g, 4.80 mmol). The mixture was warmed to reflux for 15 hours, then cooled to room temperature. Upon cooling, a white precipitate formed which was collected by filtration. The solid was triturated with diisopropyl ether followed by methylene chloride to give the title compound (0.58 g, 45%), m.p. 296–302° C. Anal. calcd. for C$_{16}$H$_{12}$ClNO: C, 71.25; H, 4.48; N, 5.19. Found: C, 70.92; H, 4.44; N, 5.04.

Example 4

Using this method, the compounds shown in Table II, III and IV were prepared. In some cases, the compounds were recrystallized from dimethyl formamide or dimethyl sulfoxide. The compounds of Table II are of the formula VIII in Table I.

TABLE II

| R¹ | R² | R³ | m.p. |
|---|---|---|---|
| H | phenyl | Me | 286–288 |
| Me | phenyl | Me | 143–144 |
| H | 4-fluorophenyl | Me | 315–318 |
| H | phenyl | n-propyl | 240–242 |
| H | phenyl | ethyl | 230–235 |
| H | phenyl | n-butyl | 208–210 |
| H | 4-methoxy-phenyl | Me | 215–225 |
| H | 4-pyridyl | Me | 340–342 |
| H | 4-carbomethoxy-phenyl | Me | HMRS (M + H): 294.1130 (calcd.) 294.1134 (found) |
| phenyl | phenyl | Me | 301–303 |
| Bn | phenyl | Me | 235–237 |
| Et | phenyl | Me | 178–179 |
| H | 2-fluorophenyl | Me | 238–239 |
| H | 3-fluorophenyl | Me | 279–281 |
| Me | 4-fluorophenyl | Me | 184–186 |
| H | 3,5-difluorophenyl | Me | 258–259 |
| H | 3,4-difluorophenyl | Me | 326–328 |
| H | 3-trifluoromethylphenyl | Me | 289–291 |
| H | 4-trifluoromethylphenyl | Me | 296–298 |
| H | 3-bromophenyl | Me | 306–309 |
| H | 2,4-difluorophenyl | Me | 281–283 |

TABLE III

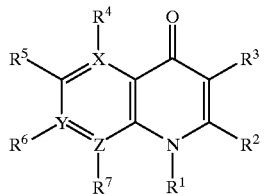

| R² | R⁴ | R⁵ | R⁶ | R⁷ | m.p. |
|---|---|---|---|---|---|
| phenyl | H | Cl | H | H | 296–302 |
| phenyl | H | H | Cl | H | 322–324 |
| phenyl | H | H | H | Cl | 166–168 |
| phenyl | Cl | H | H | H | 275–280 |
| phenyl | H | OMe | OMe | H | 290–295 |
| phenyl | H | H | H | Me | 279–281 |
| phenyl | Me | H | H | H | 162–163 |
| phenyl | H | Me | H | H | 178–179 |
| phenyl | H | H | F | H | 323–325 |
| phenyl | H | F | H | H | 310–312 |
| phenyl | F | H | H | H | 191–192 |
| phenyl | H | H | NO₂ | H | >390 |
| phenyl | H | H | NH₂ | H | 293–294 |
| phenyl | H | H | NMe₂ | H | 339–341 |
| phenyl | NO₂ | H | H | H | 230–232 |
| phenyl | NH₂ | H | H | H | 237–238 |
| phenyl | NHBn | H | H | H | 179–181 |
| 4-fluoro-phenyl | F | H | H | H | 330–332 |
| 4-fluoro-phenyl | H | Cl | H | H | 286–288 |
| 4-fluoro-phenyl | H | F | H | H | 320–323 |

TABLE IV

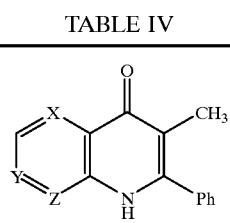

| X | Y | Z | m.p. |
|---|---|---|---|
| CH | CH | N | 260–262 |
| N | CH | CH | 258–259 |
| CH | N | CH | 330(d) |

What is claimed is:

1. A method for the treatment or prevention of an *H. pylori* infection in a host which comprises administering to said host a compound of formula I:

$$I$$

or a pharmaceutically acceptable salt or hydrate thereof, wherein:

$R^1$ is hydrogen, $C_1$–$C_3$ alkyl or phenyl which may be substituted by one to three of halo, $C_1$–$C_6$ alkyl, $C_1$–$C_6$ alkoxy, nitro, amino, $C_1$–$C_6$ alkylamino, or di($C_1$–$C_6$ alkyl)amino;

$R^2$ is ($C_1$–$C_{10}$ alkyl), ($C_1$–$C_{10}$ alkyl)phenyl, ($C_2$–$C_{10}$ alkenyl), ($C_2$–$C_{10}$ alkenyl)phenyl, ($C_2$–$C_{10}$ alkynyl), ($C_2$–$C_{10}$ alkynyl)phenyl, phenyl, naphthyl, furyl, thiophenyl or pyridyl, wherein aromatic ring portions, where present, of the foregoing $R^2$ groups may be substituted by halogen, $C_1$–$C_6$ alkyl, $C_1$–$C_6$ alkoxy, carboxy, phenyl, amino, $C_1$–$C_6$ alkylamino or di($C_1$–$C_6$ alkyl)amino;

$R^3$ is $C_1$–$C_4$ alkyl, phenyl or benzyl, said phenyl or the phenyl of said benzyl being substituted by one to three of halogen, $C_1$–$C_6$ alkyl, $C_1$–$C_6$ alkoxy, nitro, amino, $C_1$–$C_6$ alkylamino or di($C_1$–$C_6$ alkyl)amino;

$R^4$, $R^5$, $R^6$ and $R^7$ are each independently hydrogen, $C_1$–$C_3$ alkyl, $C_1$–$C_6$ alkoxy, halogen, nitro, amino, ($C_1$–$C_6$ alkyl)amino or di($C_1$–$C_6$ alkyl)amino; and X, Y and Z are each carbon with the proviso that when $R^4$, $R^5$, $R^6$ and $R^7$ are each hydrogen, then (1) if $R^3$ is methyl, $R^2$ is not $C_6$–$C_{10}$ alkenyl, propyl or phenyl, and (2) if $R^3$ is ethyl, $R^2$ is not phenyl or $C_8$–$C_{10}$ alkenyl;

in an amount effective in said treatment or prevention.

2. The method of claim 1, wherein the host is afflicted with peptic ulcers, gastritis or dyspepsia.

* * * * *